United States Patent

Finch et al.

[11] Patent Number: 5,585,376
[45] Date of Patent: Dec. 17, 1996

[54] 1,5-BENZODIAZEPINE DERIVATIVES HAVING CCK AND/OR GASTRIN ANTAGONISTIC ACTIVITY

[75] Inventors: Harry Finch; Pritom Shah; Robin A. E. Carr, all of Stevenage, United Kingdom

[73] Assignee: Glaxo Wellcome Inc., Research Triangle Park, N.C.

[21] Appl. No.: 522,363

[22] PCT Filed: Apr. 13, 1994

[86] PCT No.: PCT/EP94/01130

§ 371 Date: Oct. 30, 1995

§ 102(e) Date: Oct. 30, 1995

[87] PCT Pub. No.: WO94/24151

PCT Pub. Date: Oct. 27, 1994

[30] Foreign Application Priority Data

Apr. 15, 1993 [GB] United Kingdom .................. 9307833

[51] Int. Cl.⁶ .................. A61K 31/55; C07D 401/06; C07D 403/06
[52] U.S. Cl. ............................. 514/221; 540/518
[58] Field of Search ............................. 514/221; 540/518

[56] References Cited

FOREIGN PATENT DOCUMENTS

| 0376849 | 7/1990 | European Pat. Off. . |
| 0487207 | 5/1992 | European Pat. Off. . |
| WO-A-9113862 | 9/1991 | WIPO . |
| WO-A-9314074 | 7/1993 | WIPO . |

Primary Examiner—Philip I. Datlow
Attorney, Agent, or Firm—Bacon & Thomas

[57] ABSTRACT

The present invention relates to compounds of general formula (I)

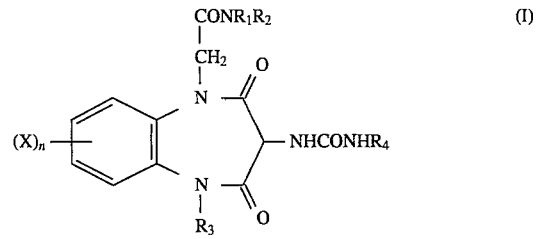

and physiologically acceptable salts thereof wherein the group $NR_1R_2$ represents a 5–7 membered saturated heterocyclic ring which may be substituted by one or two methyl groups; $R_3$ is $C_{1-6}$alkyl, $C_{3-6}$cycloalkyl or phenyl optionally substituted by 1 or 2 halogen atoms; $R_4$ is phenyl or phenyl substituted by one or two groups selected from the group consisting of halogen, $C_{1-4}$alkyl, trifluoromethyl, trifluoromethoxy or $(CH_2)_nR_5$ wherein n is zero or 1 and $R_5$ represents $C_{1-4}$alkoxy, hydroxy, nitro, cyano, $CO_2R_6$, $S(O)_pCH_3$, $NR_7R_8$, $CONR_7R_8$, $SO_2NR_7CO(C_{1-4})$alkyl, tetrazolyl, carboxamidotetrazolyl, or a 3-trifluoromethyl 1,2,4-triazolyl; $R_6$ is hydrogen, $C_{1-4}$alkyl or benzyl; $R_7$ is hydrogen or $C_{1-4}$alkyl, $R_8$ is hydrogen, $C_{1-4}$alkyl, $SO_2CH_3$ or $SO_2CF_3$, X represent hydrogen, $C_{1-4}$alkyl or halogen; m is zero, 1 or 2, and p is zero, 1 or 2. The invention also relates to processes for preparation of these compounds and to their use in medicine as antagonists of gastrin and CCK.

16 Claims, No Drawings

1,5-BENZODIAZEPINE DERIVATIVES HAVING CCK AND/OR GASTRIN ANTAGONISTIC ACTIVITY

This is a national stage application under 35USC371 of application PCT/EP94/01130, filed Apr. 13, 1994.

This invention relates to novel 1,5-benzodiazepine derivatives, to processes for their preparation, to pharmaceutical compositions containing them and to their use in medicine.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxy terminal octapeptide, CCK-8 (also a naturally-occurring neuropeptide), and 39- and 12-amino acid forms. Gastrin occurs in 34-, 17- and 14-amino acid forms, with the miniumum active sequence being the C-terminal tetrapeptide, Trp-Met-Asp-Phe-$NH_2$(CCK-4), which is the common structual element shared by both CCK and gastrin.

CCK and gastrin are gastrointestinal hormones and neurotransmitters in the neural and peripheral systems and perform their respective biological roles by binding to particular receptors located at various sites throughout the body.

There are at least two subtypes of cholecystokinin receptors termed CCK-A and CCK-B and both are found in the periphery and in the central nervous system. CCK and gastrin receptor antagonists have been disclosed for preventing and treating CCK-related and/or gastrin related disorders of the gastrointestinal and central nervous systems of animals, and more particularly humans.

U.S. Pat. No. 4,988,692 describes a group of 3-acylamino 1-alkyl-5-phenyl 1,5-benzodiazepine derivatives as cholecystokinin antagonists. Further the specification teaches that the compounds have a significantly greater affinity for the CCK-A receptor over the CCK-B receptor.

We have now found a novel group of 3-ureido 1,5-benzodiazepine compounds which are potent and specific antagonists of gastrin and/or CCK and in particular antagonists of gastrin and/or CCK at the CCK-B receptor.

The present invention thus provides compounds of the general formula (I)

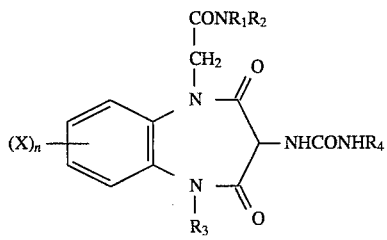

and physiologically acceptable salts thereof wherein the group $NR_1R_2$ represents a 5–7 membered saturated heterocylic ring which may be substituted by one or two methyl groups;

$R_3$ is $C_{1-6}$alkyl, $C_{3-6}$cycloalkyl or phenyl optionally substituted by 1 or 2 halogen atoms;

$R_4$ is phenyl or phenyl substituted by one or two groups selected from halogen, $C_{1-4}$alkyl, trifluoromethyl, trifluoromethoxy or $(CH_2)_nR_5$ wherein n is zero or 1 and $R_5$ represents $C_{1-4}$alkoxy, hydroxy, nitro, cyano, $CO_2R_6$, $S(O)_pCH_3$, $NR_7R_8$, $CONR_7R_8$, $SO_2NR_7CO(C_{1-4}alkyl)$, tetrazolyl, carboxamidotetrazolyl, or a 3-trifluoromethyl 1,2,4-triazolyl;

$R_6$ is hydrogen, $C_{1-4}$alkyl or benzyl;

$R_7$ is hydrogen or $C_{1-4}$alkyl, $R_8$ is hydrogen, $C_{1-4}$alkyl, $SO_2CH_3$ or $SO_2CF_3$ X represents hydrogen, $C_{1-4}$alkyl or halogen;

m is zero, 1 or 2, and p is zero, 1 or 2.

The compounds of the invention possess at least one asymmetric carbon atom and the compounds of the invention include both enantiomers and mixtures thereof including the racemate.

The term alkyl as used herein refers to both straight chain and branched chain alkyl groups. For example $C_{1-6}$alkyl includes methyl, ethyl, n-propyl, isopropyl, n-butyl, isobutyl, t-butyl or hexyl.

The term halogen includes fluorine, chlorine, bromine or iodine.

When $R_5$ represents a tetrazolyl, carboxamidotetrazolyl or 3-trifluoromethyl 1,2,4-triazolyl group these are linked to the rest of the molecule via a carbon atom therein and the invention includes all tautomers thereof and the $C_{1-4}$alkyl —N substituted derivatives thereof. Examples of such groups include (1H) tetrazol-5-yl, carboxamido-1H-tetrazol-5-yl, 2-methyltetrazol-5-yl and (3-trifluoromethyl-1,2,4-triazol-5-yl.

The group $NR_1R_2$ is linked to the rest of the molecule via the nitrogen thereof examples of such groups include pyrrolidino, piperidino, hexamethylenimino-, 2,5-dimethylpyrrolidino, 3,3-dimethylpiperidino, 2,6-dimethylpiperidino or 4,4-dimethylpiperidino.

When $R_3$ represents phenyl optionally substituted by halogen examples of such groups include phenyl optionally substituted by fluorine e.g. phenyl or 2-fluorophenyl, or 4-fluorophenyl.

When $R_3$ represents $C_{3-6}$cycloalkyl examples of such groups include cyclopropyl, cyclopentyl or cyclohexyl.

When $R_3$ represents $C_{1-6}$alkyl examples of such groups include methyl, ethyl, propyl, butyl, 3-methylbutyl or 3,3-dimethylbutyl.

Examples of suitable groups $R_4$ include phenyl optionally substituted by halogen e.g. fluorine, alkyl e.g. methyl, alkoxy e.g. methoxy, nitro, cyano, thiomethyl, carboxamido, carboxyl, dimethylamino, cyanomethyl, 1H-tetrazol-5-yl, carboxymethyl, or N-methanesulphonylcarboxamido.

A preferred class of compound according to the invention are those wherein the group $NR_1R_2$ represent pyrrolidino, piperidino, 3,3-dimethylpiperidino 4,4-dimethylpiperidino, 2,6-dimethylpiperidino or 2,5-dimethylpyrrolidino. Within this class the group $NR_1R_2$ is conveniently pyrrolidino, piperidino, or 3,3-dimethylpiperidino.

The group X is conveniently halogen e.g. bromine, fluorine or fluorine or more particularly hydrogen.

A further preferred class of compounds of formula (I) are those wherein $R_3$ is phenyl, 2-fluorophenyl or cyclohexyl and more particularly 2-fluorophenyl or cyclohexyl.

Another preferred class of compounds of formula (I) are those wherein $R_4$ is phenyl or phenyl substituted by methyl e.g. 3-methylphenyl or 3,5-dimethylphenyl, 3-dimethylaminophenyl, phenyl substituted by fluorine e.g. 4-fluorophenyl, phenyl substituted by methoxy e.g. 3-methoxyphenyl or 4-methoxyphenyl, 3-nitrophenyl, 3-cyanomethylphenyl, 3-carboxamidophenyl, 3-carboxyphenyl, 3-carboxymethylphenyl, or 3-(1H)-tetrazol-5-yl-phenyl.

A particularly preferred group of compounds according to the invention are those wherein $NR_1R_2$ represents pyrrolidino, piperidine or 3,3-dimethyl-, piperidino, $R_3$ represents 2-fluorophenyl or cyclohexyl, and X represents a hydrogen atom. Within this group particularly preferred compounds include those wherein $R_4$ is phenyl, 4-fluorophenyl, 3-dimethylaminophenyl, 3-carboxyphenyl, 3-carboxymethylphenyl or 3-(1H)-tetrazolyl-5-yl-phenyl.

A particularly preferred compound of the invention is:-
1-[1-Cyclohexyl-2,4-dioxo-5-(2-oxo-2-pyrrolidin-1-yl-ethyl)-2,3,4,5-tetrahydro-1H-benzo[b][1,4]diazepin-3-yl]-3-(4-fluoro-phenyl)urea and enantiomers thereof.

Further preferred compounds of the invention include 3-{3-[1-Cyclohexyl-2,4-dioxo-5-(2-oxo-2-pyrrolidin-1-yl-ethyl)-2,3,4,5-tetrahydro-1H-benzo[b][1,4]diazepin-3-yl]-ureido}-benzoic acid; (3-{3-[1-(2-Fluoro-phenyl)-2,4-dioxo-5-(2-oxo-2-pyrrolidin-1-yl-ethyl)-2,3,4,5-tetrahydro-1H-benzo[b][1,4]diazepin-3-yl]-ureido}-phenyl)-acetic acid; 3-{3-[1-[2-(3,3-Dimethyl-piperidin-1-yl)-2-oxo-ethyl]-5-(2-fluoro-phenyl)-2,4-dioxo-2,3,4,5-tetrahydro-1H-benzo[b][1,4]diazepin-3-yl]-ureido}-benzoic acid and enantiomers thereof.

The physiologically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

References hereinafter to a compound according to the invention includes both compounds of formula (I) and their pharmaceutically acceptable salts and solvates.

Compounds of the invention modulate the effect of gastrin and/or CCK in mammals. In particular compounds of the invention are antagonists of gastrin and/or CCK.

Compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

The preparation and use of guinea-pig isolated ileum longitudinal muscle-myenteric plexus has been described by K-H Buchheit et al in NauynSchmeideberg's Arch. Pharmacol., (1985), 329, p36–41 and by V. L. Lucaites et al in J. Pharmacol. Exp. Ther., (1991) 256,695–703.

Compounds of the invention have also been shown to have a greater affinity for the CCK-B receptor than for the CCK-A receptor. This may be determined using the CCK receptor binding assays described by Fornos et al J. Pharmacol Exp. Ther., 261 1056–1063, 1992.

Alternatively the binding affinity of compounds of the invention for CCK-A and CCK-B receptors may be determined using HeLa cell membranes that are transfected with the human CCK-B receptor or, COS-M6 cell membranes that are transiently transfected with the human CCK-A receptor.

Compounds of the invention have also been shown to be antagonists of gastrin as demonstrated by their ability to inhibit pentagastrin-stimulated acid secretion from rat isolated gastric mucosa using the procedure described by J. J. Reeves and R. Stables in *Br. J. Pharmac,*. 1985 86, p.677–684.

Compounds of the invention have also been shown to inhibit pentagastrin stimulated acid secretion in conscious gastric fistula rats using the methods described by Hedges and Parsons Journal of Physiology 1977, 267, 181–194.

The compounds of the invention are therefore useful for the treatment and/or prevention of disorders in mammals, especially humans, where modification of the effects of gastrin or CCK is of therapeutic benefit. Thus the compounds of the invention are useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. The compounds of the invention are also useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), depression, tardive dyskinesia, Parkinson's disease or psychosis. They may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 1–2000 mg per day e.g 10–500 mg per day.

The desired dose may conveniently be presented in a single dose or as divided doses administered at appropriate intervals, for example as two, three, four or more sub-doses per day.

Compounds of the invention which antagonise the function of CCK in animals, may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R_1$–$R_8$ and X are as defined for the compounds of formula (I) unless otherwise stated.

According to a first general process A, compounds of formula (I) may be prepared by the reaction of an amine of formula (II) wherein $R_1$, $R_2$, $R_3$, X and m have the meanings defined in formula (I).

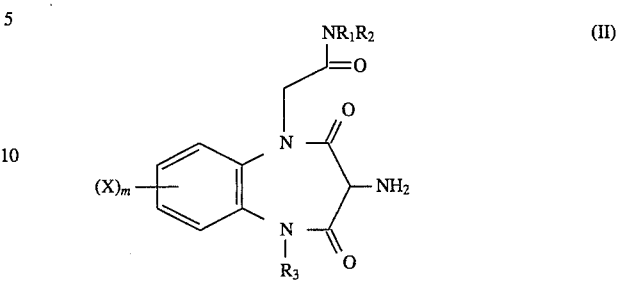

with a compound $R_4Y$, wherein $R_4Y$ is an isocyanate of formula (III), carbamoyl chloride of formula (IV), imidazolide of formula (V), or an optionally substituted phenyl carbamate of formula (VI) wherein $R_a$ is an optionally phenxoy group.

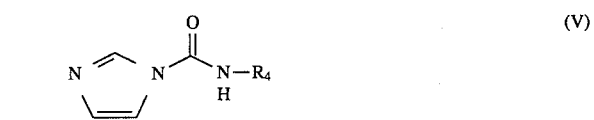

The reaction conveniently takes place in the presence of a suitable solvent such as a halohydrocarbon (e.g. dichloromethane), an ether (e.g. tetrahydrofuran) or nitrile (e.g. acetonitrile) or a mixture thereof at a temperature in the range of 0°–80° C.

Isocyanates of formula (III) may be purchased or prepared by the reaction of amines $H_2N$—$R_4$ with phosgene or triphosgene in a suitable solvent such as methylene chloride. Carbamoyl chlorides of formula (IV) are also prepared by the reaction of amines $H_2NR_4$ with phosgene or triphosgene in a suitable solvent such as methylene chloride. Imidazolides of formula (VI) are prepared by treatment of amines $H_2N$—$R_4$ with carbonyl diimidazole in a suitable solvent (dichloromethane, ether, tetrahydrofuran) at a temperature ranging from 0°–80° C. (conveniently at room temperature). Optionally substituted phenyl carbamates of formula (VI) are prepared by the reaction of amines $H_2N$—$R_4$ with the appropriate chloroformate $R_aCOCl$ in the presence of a base (pyridine, triethylamine) in a suitable solvent (dichloromethane) and at a temperature of 0°–50° C.

According to a further general process B, compounds of formula (I) may be prepared by reaction of an intermediate of formula (VII).

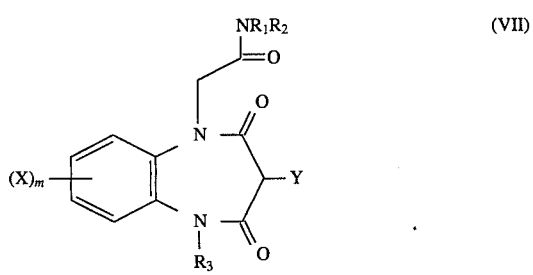

wherein Y is the group —NCO, —NHCOCl or NHCOR$_a$ wherein IR$_a$ is an optionally substituted phenoxy group or a 1-imidazole group with an amine (VIII)

and optionally in the the presence of a base such as a tertiary amine (e.g. triethylamine).

The reaction conveniently takes place in a suitable solvent such as a halogenated hydrocarbon (e.g. dichloromethane) or an ether (e.g. tetrahydrofuran) or an amide (e.g. N,N-dimethyl formamide) optionally at a temperature ranging from room temperature to the reflux temperature of the solvent.

Conveniently the compound of formula (VII) are prepared in situ from the amine (II).

In a particular aspect of the process (B) when Y is the group NHCOR$_a$ and R$_a$ is a 1-imidazole group, the imidazolide (VII) may be formed in situ in which case the amine of formula (VIII) will be mixed with the compound of formula (II)

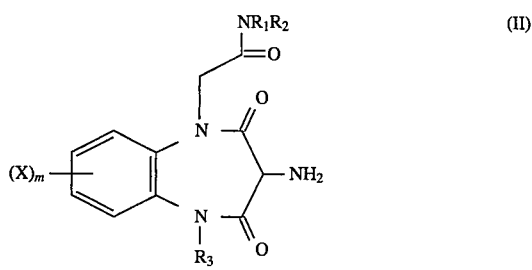

in the presence of carbonyldiimidazole under the aforementioned conditions.

For process B when Y is the group NHCOR$_a$ and R$_a$ is optionally substituted phenoxy group the reaction with the primary amine (VIII) is preferably carried out in the presence of a base such as a tertiary amine e.g. triethylamine.

For process B when Y is the isocyanate group —N=C=O the reaction with the primary amine (VIII) is preferably carried out in an aprotic solvent such as a halohydrocarbon e.g. methylene chloride. Conveniently the isocyanate is generated in situ prior to the addition of the primary amine (VIII).

The compounds of formula (VII) wherein R$_a$ is an optionally substituted phenoxy group may be prepared from the primary amine (II) by reaction with the corresponding optionally substituted phenyl chloroformate in the presence of a base such as pyridine. The reaction may be carried out in a solvent such as a halohydrocabon e.g. dichloromethane and at a temperature from 0°–500°.

Compounds of formula (VII) wherein R$_a$ is a 1-imidazole group may be prepared by reacting a compound of formula (II) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (VII) wherein Y is the isocyanate grouping —N=C=O or carbamoyl chloride —NHCOCl may be prepared from the primary amine (II) by reaction with phosgene (COCl$_2$) or triphosgene in a suitable solvent such as methylene chloride.

According to a further general process C compounds of formula (I) may also be prepared by a reaction of the compound of formula (IX)

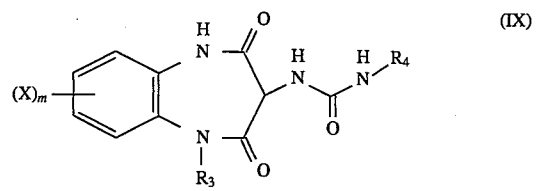

with the halide R$_2$R$_1$NCOCH$_2$Z wherein Z=a leaving group e.g. bromine, chlorine or iodine.

The reaction is conveniently carried out by treating the compound of formula (IX) with a strong base such as sodium hydride in a polar aprotic solvent such as N,N-dimethylformamide followed by reaction with the alkylating agent R$_1$R$_2$NCOCH$_2$Z.

Compounds of formula (II) may be prepared by reduction of compounds of formula (X)

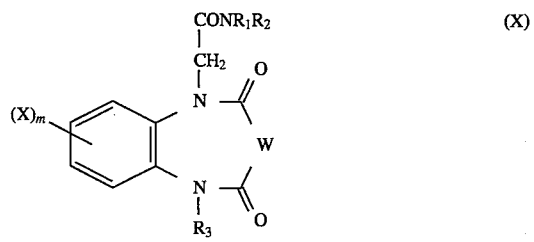

wherein W is CH—N$_3$ or C=N—NHPh.

Compounds of formula (X) wherein W is CH—N$_3$ may be reduced to a compound of formula (II) by hydrogenation in the presence of a suitable catalyst such as palladium, on a support such as carbon or calcium carbonate, or platinum (IV) oxide. The reaction conveniently takes place in the presence of a solvent such as an alkanol (e.g. ethanol) an ester (e.g. ethyl acetate) or acetic acid.

Compounds of formula (X) wherein W is C=N—NHPh may be reduced to a compound of formula (II) by reaction with zinc and acetic acid. This reaction may be carried out a temperature with the range 0°–500.

Compounds of formula (X) wherein W is CHN$_3$ may be prepared from a compound of formula (X) wherein W is CH$_2$ by treatment with a strong base such as sodium hydride or potassium tert-butoxide followed by tri-isopropyl benzenesulphonyl azide. The reaction conveniently takes place in a solvent such as an ether (e.g. tetrahydrofuran) at a temperature in the range of −78° to 20°.

Compounds of formula (X) in which W is C=NNHPh may be prepared by reaction of the ortho-phenylenediamine (XI) with the diacid chloride (XII), in a suitable solvent such as an ether e.g. tetrahydrofuran

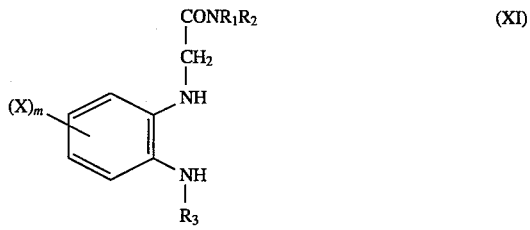

Compounds of formula (X) wherein W is CH$_2$ may be prepared by reaction of the compound of formula (XI) with the diacid chloride (XIII)

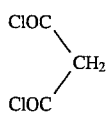

(XIII)

Compounds of formula (XI) are either known compounds or may be prepared by analogous methods. Thus for example a compound of formula (XI) may be prepared by alkylation of the amine (XIV).

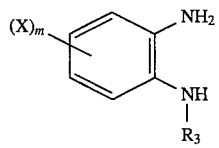

(XIV)

Thus the amine (XIV) may be reacted with the compound $R_1R_2NCOCH_2Z$, in which Z is chlorine or bromine, optionally in the presence of sodium iodide in a solvent such as N,N-dimethylformamide.

In general, the compounds of formula (III), (IV), (V) and (VI) are either known compounds or may be prepared according to methods simlar to those used for the preparation of known compounds.

According to a further process (D) a compound of formula (I) may be prepared from the compound of formula (XV) wherein $R_b$ is hydrogen

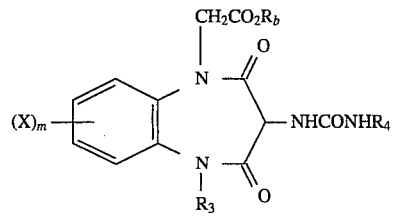

(XV)

by reaction of an activated derivative thereof with the amine $R_1R_2NH$. Conveniently the reaction is carried out using the acid in the presence of a diimide such as dicyclohexyl carbodimide and hydroxybenzotriazole in a solvent such as dichloromethane or in the presence 2-ethoxy-1-ethoxycarbonyl-1,2-dihydroquinoline in a solvent such as dimethoxyethane.

The compounds of formula (XV) wherein $R_b$ is a hydrogen may be prepared by hydrolysis of the corresponding compound of formula (XV) wherein $R_b$ is a t-butyl group, for example by reaction with trifluoroacetic acid. The compound of formula (XV) wherein $R_b$ is t-butyl may be prepared by alkylation of the corresponding compound of formula (IX) with the halo ester $Z-CH_2CO_2R_b$, wherein Z is halogen. Alternatively the compound (XV) wherein $R_b$ is t-butyl may be prepared using the general processes A and B described above for preparing the compounds of formula (I) but starting with the appropriate N-substituted benzodiazepine derivative.

According to a further process (E) a compound of formula (I) may be converted into another compound of formula (I) using conventional techniques.

Thus compounds of formula (I) wherein $R_4$ is a phenyl group substituted by a carboxyl or carboxymethyl group may be prepared by hydrolysis of the corresponding compound of formula (I) wherein $R_4$ is a phenyl group substituted by an alkoxycarbonyl or alkoxycarbonylmethyl group.

Compounds of formula (IX) may be prepared from the diamine (XIV), in which the primary amino group is protected as an p-methoxybenzyl derivative thereof, using the general procedures described above for preparing the compounds of formula (I) from the corresponding orthophenylenediamine (XI) followed by removal of the N-protecting group p-methoxybenzyl using conventional procedures.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as chiral HPLC. Alternatively the required enantiomer may be prepared from the corresponding enantiomer amine of formula (II) using any of the processes described above for preparing compounds of formula (I) from the amine (II). The enantiomers of the amine (II) may be prepared from the racemic amine (II) using conventional procedures such as salt formation with a suitably optically active acid such as R-camphorsulphonic acid or by preparative chiral HPLC.

In order that the invention may be more fully understood the following examples are given by way of illustration only.

In the Intermediates and Examples unless otherwise stated. Melting points (mp) are determined on a Gallenkamp mp apparatus and are uncorrected. All temperatures refers to °C. Column chromatography was carried out over silica gel. T.l.c. refers to thin layer chromatography on silica plates. Dried refers to solutions dried over anhydrous sodium sulphate. The following abbreviation are also used in the Examples. EA=ethyl acetate, DMF=N,N-dimethylformamide, THF=tetrahydrofuran, DE=diethyl ether, DCM=dichloromethane, MeOH=methanol, AcOH=acetic acid, ee=enantiomeric excess, $R_T$=retention time.

Intermediate 1

Cyclohexyl-(2-nitro-phenyl)-amine

A mixture of 2-chloronitrobenzene (20 g), potassium carbonate (35 g) and copper (I) iodide (1.21 g)in cyclohexylamine (43.6 ml) was heated at 150° under nitrogen for 18 h. The mixture was allowed to cool to room temperature and was adsorbed onto silica. This was chromatographed with hexane-EA (98:2) as eluent to give the title compound (22.94 g) as an orange solid.

T.l.c. (98:2 hexane-EA) Rf 0.38

Intermediate 2

N-Cyclohexyl-benzene-1,2-diamine

A solution of Intermediate 1 (10 g) in ethyl acetate (400 ml) was hydrogenated at 23° and 1 atm. pressure over 10 % palladium on carbon (1 g) for 4 h. The catalyst was removed by filtration through hyflo and the filtrate evaporated to give the title compound (8.5 g) as an orange oil.

T.l.c. (9:1 hexane-EA) Rf 0.36

Intermediate 3

2-(2-Cyclohexylamino-phenylamino)-1-pyrrolidin-1-yl-ethanone

A mixture of Intermediate 2 (8.5 g), 2-oxo-2-(pyrrolidin-1-yl)ethylbromide (9.4 g) and potassium carbonate (18.5 g) in dry DMF (250 ml) was stirred at 23° under nitrogen for 18 h. The mixture was poured into water (600 ml) and extracted with ethyl acetate (3×300 ml). The combined extracts were washed with water (3×300 ml) and saturated brine (200 ml), dried and evaporated to give a brown oil. This was chromatographed with hexane-EA (1:1) as eluent to give the title (9.8 g) as a cream solid, m.p.108°–110°.

T.l.c. (1:1 hexane-EA) Rf 0.42

Intermediate 4

1-Cyclohexyl-5-(2-oxo-2-pyrrolidin-1-yl-ethyl)-3-(phenyl-hydrazono)-1,5-dihydrobenzo[b][1.4]diazepine-2,4-dione Solutions of Intermediate 3 (9.8 g) and 2-(phenyl-hydrazono)-propanedioyl dichloride (8.36 g) in dry THF (75 ml) were added at equal rates to dry THF (75 ml) cooled to −10° under nitrogen. When the addition was complete the mixture was allowed to warm to room temperature and stir for 3 h. The solvent was removed by evaporation to give the crude title-compound (19.5 g) as a yellow crunchy foam.

T.l.c. (DE) Rf 0.23

Intermediate 5

3-Amino-1-cyclohexyl-5-(2-oxo-2-pyrrolidin-1-yl-ethyl)-1,5-dihydrobenzo[b][1,4]diazepine-2,4-dione A solution of Intermediate 4 (19 g) in glacial acetic acid (200 ml) was added dropwise to a stirring suspension of zinc dust (15 g) in glacial acetic acid. The mixture was stirred at 230 for 1.5 h whereupon the zinc was removed by filtration through hyflo and the filtrate evaporated to give a red oil. This was partitioned between water (200 ml) and ethyl acetate (75 ml). The aqueous portion was adjusted to pH9 with solid $Na_2CO_3$ and extracted with ethyl acetate (4×100 ml). The combined organic extracts were dried and evaporated to give a brown oil which was chromatographed with DCM-MeOH (95:5) as eluent to give the title (7.4 g) as a pink crunchy foam.

T.l.c. (95:5 DCM-MeOH) Rf 0.26

Intermediate 6

3-{3-[-1-Cyclohexyl-2,4-dioxo-5-(2-oxo-2-pyrrolidin-1-yl-ethyl)-2,3,4,5-1H-benzo[b][1,4]diazepin-3-yl]-ureido}-benzoic acid,benzyl ester Triethylamine (108 µl) and triphosgene (77 mg) were added sequentially to a solution of 3-amino-benzoic acid benzyl ester (177 mg) in dry THF (1 0 ml) at 0° under nitrogen. More triethylamine (108 µl) was added and stirring continued at 0° for 30 min. A solution of Intermediate 5 (250 mg) in dry THF (10 ml) was added and stirring continued at 23° for 18 h. The mixture was then partitioned between 2N hydrochloric acid (50 ml) and ethyl acetate (50 ml). The dried organic extract was evaporated and the residue chromatographed with EA-hexane (2:1) as eluent to give the title compound (320 mg) as a pale yellow solid.

T.l.c. (2:1 EA-hexane) Rf 0.17

I.r. (Solution in $CHCl_3$)3384;2939;1690;1658;1423 $cm^1$

Intermediate 7

3-Nitro-benzoic acid tert-butyl ester

A solution of 3-nitrobenzoic acid (1.4 g) in dry toluene (10 ml) was treated with N,N-dimethylformamide di-tert-butyl acetal (10 ml). The mixture was heated under reflux for 18 h then cooled, diluted with ethyl acetate and washed consecutively with water, 8% sodium bicarbonate solution and saturated brine. The dried organic phase was evaporated to give the title compound (1.02 g) as a yellow oil.

T.l.c. (97:3 DCM-MeOH) Rf 0.66

Intermediate 8

3-Amino-benzoic acid tert-butyl ester

A solution of Intermediate 7 (1 g) in ethanol (20 ml) was hydrogenated at 23° and 1 atm pressure in the presence of 10% palladium on carbon as catalyst (200 mg). After 2 h the mixture was filtered through hyflo and the filtrate evaporated. The residue was chromatographed with DCM-MeOH (97:3) as eluent to give the title compound (727 mg) as a colourless oil.

T.l.c. (97:3 DCM-MeOH) Rf 0.35 lntermediate 9

(3- Nitro-phenyl)-acetic acid benzyl ester,

A mixture of 3-nitrophenylacetic acid (5 g), benzyl alcohol (2.9 ml) and 4,4-dimethylaminopyridine (300 mg) in dry dichloromethane (50 ml) was treated with 1-(3-dimethylaminopropyl)-3-ethylcarbodiimide (7.4 g). The resulting yellow mixture was stirred at 23° for 3 days whereupon the solvent was removed in vacuo. The residue was partitioned between water (100 ml) and ethyl actate (100 ml) and the organic phase washed with water (2×100 ml) and saturated brine (100 ml) then dried and evaporated. The residue was chromatographed with hexane-EA (4:1) as eluent then again with isohexane-DCM (1:1) as eluent to give the title compound (2.05 g) as a pale yellow oil.

T.l.c. (4:1 hexane-EA) Rf 0.35

Intermediate 10

(3-Amino-phenyl)-acetic acid benzyl ester

A solution of Intermediate 9 (2.05 g) in ethyl acetate (100 ml) was hydrogenated at 23° and 1 atm pressure in the presence of 5% platinum on carbon (200 mg) as catalyst. After 90 min the mixture was filtered through hyflo and the filtrate evaporated to give the title compound (1.77 g) as a pale yellow oil T.l.c. (DCM) Rf 0.35

Intermediate 11

(2-Fluoro-phenyl)-(2-nitro-phenyl)-amine

A mixture of 2-fluoroaniline (5.0 g), potassium carbonate (2.5 g) and copper(I)iodide (414 mg) in 2-fluoronitrobenzene (16.9 ml) was heated to 180° under nitrogen for 18 h. The cooled mixture was poured into water (300 ml) and extracted with ethyl acetate (2×250 ml) then the combined extracts were washed with saturated brine and evaporated. The residual brown oil was azeotroped with ethanol/water then toluene. The residue was chromatographed with hexane-DE (100:0 to 95:5) to give the title compound (3.25 g) as a bright orange solid, m.p.58°–9°.

T.l.c.(95:5 hexane-DE) Rf 0.45

Intermediate 12

N-(2-Fluoro-phenyl)-benzene-1,2-diamine

A solution of Intermediate 11(15.6 g)in ethyl acetate (400 ml) was hydrogenated at 23° and 1 atm pressure in the presence of 5% platinum on carbon (2 g) as catalyst. After 1 h the mixture was filtered through hyflo and the filtrate evaporated to give the title compound (13.45 g) as a yellow solid.

.T.l.c. (9:1 hexane-DE) Rf 0.25

Intermediate 13

2-[2-(2-Fluoro-phenylamino)-phenylamino]-1-pyrrolidin-1-yl-ethanone

A solution of 2-oxo-2-(pyrrolidin-1-yl)ethylbromide (12.8 g) in dry DMF (60 ml) was added dropwise to a mixture of Intermediate 12 (13.45 g) and potassium carbonate (27.5 g) in dry DMF (100 ml) at 23° under nitrogen. The mixture was stirred at 60° for 4 h then poured into 2N sodium carbonate solution (500 ml) and extracted with ethyl acetate (400 ml). The organic extract was washed with water (2×250 ml) and .saturated brine (250 ml), dried and evaporated. The residue was chromatographed with hexane-DE (50:50 to 0:100) as eluent to give the title compound (14.12 g) as a pale brown solid.

T.l.c. (DE) Rf 0.53

Intermediate 14

1-(2-Fluoro-phenyl)-5-(2-oxo-2-pyrrolidin-1-yl-ethyl)-3-(phenyl-hydrazono)-1,5-dihydro-benzo[b][1.4]diazepine-2,4-dione Solutions of Intermediate 13 (14.12 g) and 2-(phenyl-hydrazono)-propanedioyl dichloride (11.04 g) in dry THF (100 ml) were added simultaneously and dropwise at equal rates to dry THF (100 ml) cooled to −10° under nitrogen. When the addition was complete the mixture was allowed to warm to room temperature and stir for 3.5 h. The solvent was removed by evaporation to give the crude title compound (23 g) as a yellow crunchy foam.

T.l.c. (EA) Rf 0.5

Intermediate 15

3-Amino-1-(2-fluoro-phenyl)-5-(2-oxo-2-pyrrolidin-1-yl-ethyl)-1,5-dihydrobenzo[b][1.4]diazepine-2,4-dione A solution of Intermediate 14 (23 g) in glacial acetic acid (200 ml) was added dropwise to a stirred suspension of zinc dust (22.2 g) in glacial acetic acid (100 ml) in a cold water-bath. The mixture was stirred at 23° for 2.5 h whereupon the zinc was removed by filtration through hyflo and the filtrate evaporated. The residue was partitioned between water (150 ml) and ethyl acetate (100 ml) and the aqueous portion basified with solid $Na_2CO_3$. The layers were separated and the aqueous phase further extracted with ethyl acetate then the combined organic extracts were washed with saturated brine, dried and evaporated. The residue was chromatographed with EA-MeOH (100:0 to 95:5) as initial eluent followed by DCM-MeOH (80:20) to give the title compound (11.07 g) as a fawn powder.

T.l.c. (95:5 DCM MeOH) Rf 0.23

Intermediate 16

(3-{3-[1-(2-Fluoro-phenyl)-2,4-dioxo-5-(2-oxo-2-pyrrolidin-1-yl-ethyl)-2,3,4,5-tetrahydro-1H-benzo[b][1,4]diazepin-3-yl]-ureido}-phenyl)-acetic acid benzyl ester A solution of Intermediate 15 (3 g) in dry dichloromethane (40 ml) was added dropwise to a stirred solution of phosgene in toluene (60 ml) under nitrogen. The resulting mixture was stirred at 23° for 4 h then nitrogen was bubbled through the mixture into ammonia solution for 18 h. The mixture was then evaporated and the residue dried at 60° in vacuo for 3 h to give the intermediate isocyanate (3.3 g) as a buff solid which was used without further characterisation. A solution of this isocyanate (400 mg) in dry dichloromethane (3 ml) was added dropwise to a stirred solution of (3-amino-phenyl)-acetic acid benzyl ester (241 mg) in dry dichloromethane (2 ml) at 23° under nitrogen. After 60 min the solvent was removed in vacuo and the residue triturated with diethyl ether. The solid was filtered off and dried to give the title compound (263 mg) as an off-white solid, m.p.104°–6°.

T.l.c. (EA) Rf 0.54

Intermediate 17

2-Bromo-1-(3,3-dimethyl-piperidin-1-yl)-ethanone

A mixture of 3,3-dimethylpiperidine (10 g) and triethylamine (12.3 ml) in dry dichloromethane (50 ml) was added dropwise to an ice-cold solution of bromoacetyl bromide (7.7 ml) in dry dichloromethane (100 ml). The mixture was stirred at 23° for 18 h then recooled to 0°. Iced water (200 ml) was added and the layers separated. The aqueous layer was further extracted with dichloromethane (2×200 ml) then the combined extracts were washed with 2N HCl (200 ml) and saturated brine (200 ml), dried and evaporated to give the title compound (17.28 g) as a brown oil.

T.l.c. (DE) Rf 0.49

Intermediate 18

1-(3,3-Dimethyl-piperidin-1-yl)-2-[2-(2-fluoro-phenylamino)-phenylamino]-ethanone A mixture of Intermediate 12 (3 g)) and potassium carbonate (6.15 g) in dry DMF (10 ml) was treated with a solution of 2-bromo-1-(3,3-dimethyl-piperidin-1-yl)-ethanone (3.5 g) in dry DMF (10 ml) and stirred at 23° under nitrogen for 3 days. The mixture was poured into water and extracted with ethyl acetate. The combined extracts were washed with water and saturated brine, dried and evaporated to give a brown oil. This was chromatographed with DCM-MeOH (100:0 to 97:3) as eluent to give the title compound (3.17 g) as a pale brown foam.

T.l.c. (DCM) Rf 0.23

Intermediate 19

1-[2-(3,3-Dimethyl-piperidin-1-yl)-2-oxo-ethyl]-5-(2-fluoro-phenyl)-3-(phenylhydrazono)-1,5-dihydro-benzo[b][1,4]diazepine-2,4-dione Solutions of Intermediate 18 (3.08 g) and 2-(phenylhydrazono)-propanedioyl dichloride (2.12 g) in dry THF (100 ml) were added at equal rates to dry THF (50 ml) cooled to −10° under nitrogen. When the addition was complete the mixture was allowed to warm to room temperature and stirred for 2 h. The solvent was removed by evaporation to give the crude title compound (5.25 g) as a yellow crunchy foam.

T.l.c. (95:5 DCM-MeOH) Rf 0.68

Intermediate 20

3-Amino-1-[2-(3,3-dimethyl-piperidin-1-yl)-2-oxo-ethyl]-5-(2-fluoro-phenyl)-1,5-dihydro-benzo[b][1.4]diazepine-2,4-dione A solution of Intermediate 19 (5.15 g) in glacial acetic acid (75 ml) was added dropwise to a stirring suspension of zinc dust (4.47 g) in glacial acetic acid (50 ml) in a cold water-bath. The mixture was stirred at 23° for 6 h whereupon the zinc was removed by filtration through hyflo and the filtrate evaporated. The residue was partitioned between water and ethyl actate and the aqueous portion basified with solid $Na_2CO_3$. The organic extract was washed with saturated brine, dried and evaporated. The residue was chromatographed with DCM-MeOH (95:5) as eluent to give the title compound (2.38 g) as a pale brown solid.

T.l.c. (95:5 DCM-MeOH) Rf 0.18

Intermediate 21

3-{3-[1-[2-(3,3-Dimethyl-piperidin-1-yl)-2-oxo-ethyl]-5-(2-fluoro-phenyl)-2,4-dioxo-2,3,4,5-tetrahydro-1H-benzo[b][1,4]diazepin-3-yl]-ureido}-benzoic acid tert-butyl ester Triethylamine (0.31 ml) and triphosgene (217 mg) were added sequentially to a solution of 3-amino-benzoic acid tert-butyl ester (423 mg) in dry THF (10 ml) at 0° under nitrogen. More triethylamine (0.31 ml) was added and stirring continued at 0° for 30 min. A solution of Intermediate 20 (800 mg) in dry THF (10 ml) was added and stirring continued at 23° for 18 h. The mixture was then partitioned between phosphate buffer solution (pH6.5) and dichloromethane. The combined organic extracts were washed with saturated brine, dried and evaporated and the residue chromatographed with DCM-MeOH (97:3) as eluent to give a pale green solid which was triturated with DE-hexane (1:1) to give the title compound (1.07 g) as a white solid, m.p. 170°.

T.l.c. (97:3 DCM-MeOH) Rf 0.15

EXAMPLE 1

1-[1-Cyclohexyl-2,4-dioxo-5-(2-oxo-2-pyrrolidin-1-yl-ethyl)-2,3,4,5-tetrahydro-1H-benzo[b][1.4]diazepin-3-yl]-3-(4-fluoro-phenyl)urea 4-Fluorophenyl isocyanate (650 μl) was added to a solution of Intermediate 5 (2 g) in dry dichloromethane (50 ml) at 23° under nitrogen. The resulting mixture was stirred for 1 h then adsorbed onto silica and chromatographed with EA-MeOH (100:0 to 95:5) as eluent to give the title compound (1.92 g) as a white solid, m.p. 181°–3°.

T.l.c. (EA) Rf 0.42

The compound of Example 1 (1.7 g) was separated into its 2 enantiomers (Isomer 1 and Isomer 2) by chiral HPLC.

Column: Chiralcel OD 25 cm×20 mm id
Eluent: Hexane-EtOH (70:30)
Flow rate: 20 ml min$^{-1}$
Detection: uv@254 nm
Isomer 1, (452 mg) as a white solid - R$_T$8.6 min. H.p.l.c. >99.5% ee
T.I.c. (EA) Rf 0.42
I.r. (Solution in CHCl$_3$) 3622;3091;2938;2895;2403;1657;1515;1425;1189; 1047;929 cm$^{-1}$
Isomer 2, (488 mg) as a white solid- R$_T$15.1 min. H.p.l.c. 98.8%ee
T.I.c. (EA) Rf 0.42
I.r. (KBr disc) 3366;2935;1695;1657;1558;1510;1422;1206;833;763 cm$^{-1}$

EXAMPLE 2

3-{3-[1-Cyclohexyl-2,4-dioxo-5-(2-oxo-2-pyrrolidin-1-yl-ethyl)-2,3,4,5-tetrahydro-1H-benzo[b][1.4]diazepin-3-yl]- ureido}-benzoic acid A solution of Intermediate 6 (248 mg) in ethyl acetate (10 ml) and THF (5 ml) was hydrogenareal at 23° and 1 atm pressure overnight in the presence of 10% palladium on carbon (25 mg) as catalyst. More catalyst (25 mg) was added and hydrogenation continued for 2 h whereupon the mixture was filtered through hyflo and the filtrate evaporated to give the title compound (216 mg) as a white solid, m.p.275°–6°.

T.I.c. (100:2 EA-AcOH) Rf 0.25
I.r. (KBr disc) 3369;2935;1700;1659;1557;1499;1431;1233;760 cm$^{-1}$ (3-{3-[1-(2-Fluoro-phenyl)-2,4-dioxo-5-(2-oxo-2-pyrrolidin-1-yl-ethyl)-2,3,4,5-tetrahydro-1H-benzo[b][1,4]diazepin-3-yl]-ureido}-phenyl)-acetic acid A solution of Intermediate 16 (177 mg) in THF (10 ml) was hydrogenated at 23° and 1 atm pressure in the presence of 10% palladium on carbon (10 mg) as catalyst. After 90 min the mixture was filtered through hyflo and the filtrate evaporated to give the title compound (67 mg) as a white solid, m.p. 197°–9°.

T.I.c. (EA) Rf 0.17
I.r. (KBr disc) 3331;1708;1651;1562;1499;1454;1403;1238;761 cm$^{-1}$

EXAMPLE 4

3-{3-[1-[2-(3,3-Dimethyl-piperidin-1-yl)-2-oxo-ethyl]-5-(2-fluoro-phenyl)-2,4-dioxo-2,3,4,5-tetrahydro-1H-benzo[b][1,4]diazepin-3-yl]-ureido}-benzoic acid A solution of Intermediate 21 (400 mg) indichloromethane (20 ml) was treated with trifluoroacetic add (2 ml) and stirred at 23° under nitrogen for 1 h. The mixture was concentrated in vacuo and the residue chromatographed with DCM-MeOH (95:5) as eluent to give the title compound (344 mg) as a white solid, m.p.225° dec.

T.I.c. (95:5 DCM-MeOH) Rf 0.26

Using the general processes A, B, C and D described above the following compounds of the invention have also been prepared.

TABLE 1

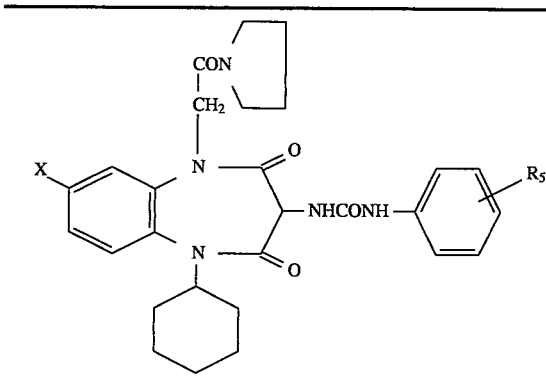

| Ex. No | X | R$_5$ | mp | Process |
|---|---|---|---|---|
| 5 | H | 3,5-diCH$_3$ | 254–5° | A |
| 6 | H | 4-OCH$_3$ | 180–2° | A |
| 7 | H | 3-F | 188–90° | A |
| 8 | H | 3-NO$_2$ | 173–5° | A |
| 9 | H | 3-CH$_2$CN | 210–2° | A |
| 10 | H | H | 216–8° | A |
| 11 | H | 3-CONH$_2$ | 275–7° | A |
| 12 | H | 3-N(CH$_3$)$_2$ | 251–3° | A |
| 13 | Br | 4-F | *Rf 0.3 | D |

*T.I.c. cyclohexane:E A:AcOH 1:1:0.0.4

TABLE 2

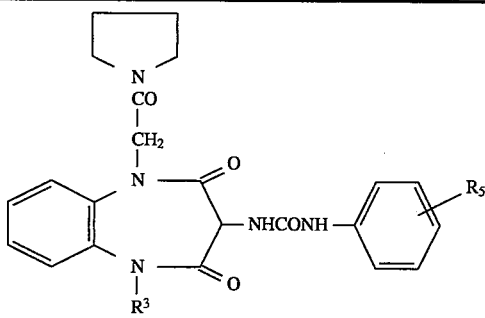

| Ex. No | R$_3$ | R$_5$ | mp | Process |
|---|---|---|---|---|
| 14 | Ph | 3-tetrazolyl | 243° | A |
| 15 | Ph | 3-CH$_3$ | 234–6° | A |
| 16 | Ph | 3-CONHSO$_2$CH$_3$ | 199–200° | B |
| 17 | 2-F-Ph | 4-F | 155–7° | A |

TABLE 2-continued

[Structure: benzodiazepine with N-CO-CH2-N(pyrrolidine), NHCONH-phenyl-R5, N-R3]

| Ex. No | R3 | R5 | mp | Process |
|---|---|---|---|---|
| 18 | 2F-Ph | 3-CH₃ | 195–7° | A |
| 19 | 2F-Ph | 3-CO₂H | −225–7° | B |

TABLE 3

[Structure: benzodiazepine with NR1R2-CO-CH2-N, NHCONH-phenyl-F, N-(2-F-phenyl)]

| Ex. No. | NR₁R₂ | mp | Process |
|---|---|---|---|
| 20 | 4-methylpiperidinyl | 240° | A |
| 21 | 4,4-dimethylpiperidinyl | 170° | A |
| 22 | pyrrolidinyl | 260° | A |
| 23 | piperidinyl | 220–5° dec | C |
| 24 | azepanyl | 255–8° | D |

Pharmacy Examples
Tablets

| a. | Active ingredient | 50 mg |
|---|---|---|
| | Lactose anhydrous USP | 163 mg |
| | Microcrystalline Cellulose NF | 69 mg |
| | Pregelatinised starch Ph.Eur. | 15 mg |
| | Magnesium stearate USP | 3 mg |
| | Compression weight | 300 mg |

The active ingredient, microcrystalline cellulose, lactose and pregelatinised starch are sieved through a 500 micron sieve and blended in a suitable mixer. The magnesium stearate is sieved through a 250 micron sieve and blended with the active blend. The blend is compressed into tablets using suitable punches.

| b. | Active ingredient | 50 mg |
|---|---|---|
| | Lactose monohydrate USP | 120 mg |
| | Pregelatinised starch Ph.Eur. | 20 mg |
| | Crospovidone NF | 8 mg |
| | Magnesium stearate USP | 2 mg |
| | Compression weight | 200 mg |

The active ingredient, lactose and pregelatinised starch are blended together and granulated with water. The wet mass is dried and milled. The magnesium stearate and Crospovidone are screened through a 250 micron sieve and blended with the granule. The resultant blend is compressed using suitable tablet punches.

Capsules

| a. | Active ingredient | 50 mg |
|---|---|---|
| | Pregelatinised Starch Ph.Eur. | 148 mg |
| | Magnesium stearate USP | 2 mg |
| | Fill weight | 200 mg |

The active ingredient and pregelatinised starch are screened through a 500 micron mesh sieve, blended together and lubricated with magnesium stearate (meshed through a 250 micron sieve). The blend is filled into hard gelatin capsules of a suitable size.

| b. | Active ingredient | 50 mg |
|---|---|---|
| | Lactose monohydrate USP | 223 mg |
| | Povidone USP | 12 mg |
| | Crospovidone NF | 12 mg |
| | Magnesium stearate | 3 mg |
| | Fill weight | 300 mg |

The active ingredient and lactose are blended together and granulated with a solution of Povidone. The wet mass is dried and milled, The magnesium stearate and Crospovidone are screened through a 250 micron sieve and blended with the granule. The resultant blend is filled into hard gelatin capsules of a suitable size.

CCK-B, Receptor Binding Affinity

CCK-B receptor binding studies were carried out using HeLa cell membranes which had been stably transfected with the human CCK-B receptor cloned from temporal cortex cDNA library.

19

Measurement of CCK-B binding affinity.

The transfected HeLa cell membranes were incubated with 30 pM [$^{125}$I]BH-sCCK-8 in the presence of various concentrations of the test compound (1 pM to 1 μM). All experiments were performed in an assay volume of 250 μl. Membranes were harvested onto GF/C glass fibre filter paper (Whatman, UK) by rapid filtration using a Cell Harvester (Brandel model M-24R) and washed three times with HEPES Wash buffer chilled to 4° C. The radioactivity trapped on individual filter discs was counted over 60 seconds using a gamma counter (Mini Gamma counter, LKB, Wallac, Finland) at a counting efficiency of 77%. A control experiment was also carried out in the absence of a test compound.

Analysis of the data was performed by computer-assisted non-linear regression (ALLFIT programmes DeLean et al., 1978;). IC$_{50}$ values for the test compounds were convened to K$_i$ values using the Cheng & Prussof equation (K$_i$=IC$_{50}$/(1+[L]/K$_D$)) (Cheng and Prussof, 1973). Results obtrained with representative compounds of the invention in this test are given below and expressed as pKi values.

CCK-A Receptor Binding Affinity

CCK-A receptor binding studies were carried out using COS-M6 cell membranes which have been transiently transfected with human gall bladder CCK-A receptor cDNA.

The clone was transiently transfected into COS-M6 cells grown to 80% confluency using the dimethylaminoethyl-dextran method based on the method of Seed and Araffo. Proc. Natl, Acad, Sci. USA 84, 3365 1987. The required transfected cell membranes were then isolated in a conventional manner.

The affinity of compounds of the invention for the CCK-A receptor was determined using the procedures described above for the CCK-B receptor however, in these experiments the test compound was tested at concentrations in the range 10 pM to 10 μM.

CCK-B Binding Studies

| Example No | pKi |
|---|---|
| 1 | 8.5 |
| 1 (isomer 1) | 8.5 |
| 1 (isomer 2) | 8.1 |
| 2 | 8.7 |
| 3 | 8.4 |
| 4 | 8.8 |
| 7 | 8.3 |
| 8 | 8.6 |
| 10 | 8.4 |
| 12 | 9.0 |
| 14 | 8.5 |
| 15 | 8.8 |
| 20 | 8.7 |

The compounds of the invention are essential non-toxic a theraapeutically active doses. Thus no untoward effects were observed when the compound of Example 1 (isomer 1) was administered to the gastrin fistula rat of doses of 0.3 and 1 mg/kg iv at these doses gastric acid secretion was significally inhibited.

We claim:

1. Compounds of the formula (I)

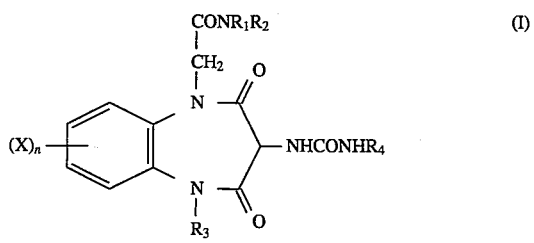

and physiologically acceptable salts thereof wherein the group NR$_1$R$_2$ represents a 5–7 membered saturated heterocylic ring which may be substituted by one or two methyl groups;

R$_3$ is C$_{1-6}$alkyl, C$_{3-6}$cycloalkyl or phenyl optionally substituted by 1 or 2 halogen atoms;

R$_4$ is phenyl or phenyl substituted by one or two groups selected from halogen, C$_{1-4}$ alkyl, trifluoromethyl, trifluoromethoxy or (CH$_2$)$_n$R$_5$ wherein n is zero or 1 and R$_5$ represents C$_{1-4}$alkoxy, hydroxy, nitro, cyano, CO$_2$R$_6$, S(O)$_p$CH$_3$, NR$_7$R$_8$, CONR$_7$R$_8$, SO$_2$NR$_7$CO(C$_{1-4}$alkyl), tetrazolyl, carboxamidotetrazolyl, or a 3-trifluoromethyl 1,2,4-triazolyl;

R$_6$ is hydrogen, C$_{1-4}$alkyl or benzyl;

R$_7$ is hydrogen or C$_{1-4}$alkyl,

R$_8$ is hydrogen, C$_{1-4}$alkyl, SO$_2$CH$_3$ or SO$_2$CF$_3$,

X represents hydrogen, C$_{1-4}$alkyl or halogen;

m is zero, 1 or 2, and p is zero, 1 or 2.

2. Compounds as claimed in claim 1 wherein NR$_1$R$_2$ represents pyrrolidino, 2,5-dimethylpyrrolidino, piperidino, 3,3-dimethylpiperidino, 4,4-dimethylpiperidino or 2,6-dimethylpiperidino.

3. Compounds as claimed in claim 1 wherein NR$_1$R$_2$ represents pyrrolidino.

4. Compounds as claimed in claim 1 wherein R$_3$ represents phenyl, 2-fluorophenyl or cyclohexyl.

5. Compounds as claimed in claim 1 wherein R$_3$ represents cyclohexyl.

6. Compounds as claimed in claim 1 wherein R$_4$ represents phenyl, 3-methylphenyl, 3,5-dimethylphenyl, 3-dimethylaminophenyl, 4-fluorophenyl, 3-methoxyphenyl, 4-methoxyphenyl, 3-nitrophenyl, 3-cyanomethylphenyl, 3-carboxamidophenyl, 3-carboxyphenyl, 3-carboxymethylphenyl or 3-(1H)-tetrazol-5-yl-phenyl.

7. Compounds as claimed in claim 1 wherein R$_4$ represent phenyl, 4-fluorophenyl, 3-dimethylaminophenyl, 3-carboxylphenyl, 3-carboxymethylphenyl or 3-(1H)-tetrazol-5-yl-phenyl.

8. 1-[1-Cyclohexyl-2,4-dioxo-5-(2-oxo-2-pyrrolidin-1-yl-ethyl)-2,3,4,5-tetrahydro-1H-benzo[b][1,4]diazepin-3-yl]-3-(4-fluoro-phenyl)urea and enantiomers thereof.

9. A compound selected from

3-{3-[1-Cyclohexyl-2,4-dioxo-5-(2-oxo-2-pyrrolidin-1-yl-ethyl)-2,3,4,5-tetrahydro-1H-benzo[b][1,4]diazepin-3-yl]-ureido}-benzoic acid;

(3-{3-[1-(2-Fluoro-phenyl)-2,4-dioxo-5-(2-oxo-2-pyrrolidin-1-yl-ethyl)-2,3,4,5-tetrahydro-1H-benzo[b][1,4]diazepin-3-yl]-ureido}-phenyl)-acetic acid;

3-{3-[1-[2-(3,3-Dimethyl-piperidin-1-yl)-2-oxo-ethyl]-5-(2-fluoro-dioxo-2,3,4,5-tetrahydro-1H-benzo[b][1,4]diazepin-3-yl]-ureido}-benzoic acid, and enantiomers thereof.

10. Compounds as defined in claim 1 for use in therapy.

11. A pharmaceutical composition comprising a compound as defined in claim 1 in admixture with one or more physiologically acceptable carriers or excipients.

12. A method of treatment of a mammal including man for conditions where modifications of the effects of gastrin and/or CCK is of therapeutic benefit comprising administration of an effective amount of a compound as defined in claim 1.

13. A pharmaceutical composition comprising a compound as claimed in claim 8 in admixture with one or more physiologically acceptable carriers or excipients.

14. A method of treatment of a mammal including man for conditions where modifications of the effects of gastrin and/or CCK is of therapeutic benefit comprising administration of an effective amount of a compound as claimed in claim 8.

15. Compounds as claimed in claim 1 wherein:

$NR_1R_2$ represents pyrrolidino, 2,5-dimethylpyrrolidino, piperidino, 3,3-dimethylpiperidino, 4,4-dimethylpiperidino or 2,6-dimethylpiperidino;

$R_3$ represents phenyl, 2-fluorophenyl or cyclohexyl; and $R_4$ represents phenyl, 3-methylphenyl, 3,5-dimethylphenyl, 3-dimethylaminophenyl, 4-fluorophenyl, 3-methoxyphenyl, 4-methoxyphenyl, 3-nitrophenyl, 3-cyanomethylphenyl, 3-carboxamidophenyl, 3-carboxylphenyl, 3-carboxymethylphenyl or 3-(1H)-tetrazol-5-yl-phenyl.

16. Compounds as claimed in claim 1 wherein:

$NR_1R_2$ represents pyrrolidino, piperidino, or 3,3-dimethylpiperidino;

$R_3$ represents 2-fluorophenyl or cyclohexyl;

X represents hydrogen; and $R_4$ represents phenyl, 4-fluorophenyl, 3-dimethylaminophenyl, 3-carboxyphenyl, 3-carboxymethylphenyl or 3-(1H)-tetrazol-5-yl-phenyl.

* * * * *